(12) United States Patent
Miller et al.

(10) Patent No.: US 7,074,430 B2
(45) Date of Patent: *Jul. 11, 2006

(54) CONTROLLED RELEASE TRAMADOL TRAMADOL FORMULATION

(75) Inventors: Ronald Brown Miller, Basel (CH); Sandra Therese Antoinette Malkowska, Cambridgeshire (GB); Walter Wimmer, Limburg (DE); Udo Hahn, Nentershausen (DE); Stewart Thomas Leslie, Cambridge (GB); Kevin John Smith, Cambridge (GB); Horst Winkler, Linter (DE); Derek Allan Prater, Cambridge (GB)

(73) Assignee: Euro-Celtique S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 09/800,204

(22) Filed: Mar. 6, 2001

(65) Prior Publication Data

US 2001/0036477 A1    Nov. 1, 2001

Related U.S. Application Data

(63) Continuation of application No. 08/677,798, filed on Jul. 10, 1996, now Pat. No. 6,254,887, which is a continuation of application No. 08/241,129, filed on May 10, 1994, now Pat. No. 5,591,452.

(51) Int. Cl.
*A61K 9/22* (2006.01)

(52) U.S. Cl. ............... 424/468; 424/470; 424/480; 424/488; 424/494; 424/495; 424/499; 424/502; 424/424; 514/646

(58) Field of Classification Search ............ 424/468, 424/470, 476, 480, 488, 444, 445, 498, 499, 424/502; 514/646
See application file for complete search history.

(56) References Cited

U.S. PATENT DOCUMENTS

| | | | |
|---|---|---|---|
| 2,738,303 A | 3/1956 | Blythe et al. .............. 167/82 |
| 3,065,143 A | 11/1962 | Christenson et al. ......... 167/82 |
| 3,652,589 A | 3/1972 | Flick et al. .......... 260/326.5 M |
| 3,830,934 A | 8/1974 | Flick et al. ................. 424/330 |
| 3,845,770 A | 11/1974 | Theeuwes et al. .......... 128/260 |
| 3,950,508 A | 4/1976 | Mony et al. ................ 424/19 |
| 3,965,256 A | 6/1976 | Leslie .......................... 424/22 |
| 3,974,157 A | 8/1976 | Shetty et al. ......... 260/247.2 B |
| 4,013,784 A | 3/1977 | Speiser ........................ 424/19 |
| 4,063,064 A | 12/1977 | Saunders et al. ............ 219/121 |
| 4,076,798 A | 2/1978 | Casey et al. ................ 424/22 |
| 4,088,864 A | 5/1978 | Theeuwes et al. .......... 219/121 |
| 4,132,753 A | 1/1979 | Blichare et al. .............. 264/25 |
| 4,259,314 A | 3/1981 | Lowey ........................ 424/19 |
| 4,343,789 A | 8/1982 | Kawata et al. .............. 424/78 |
| 4,366,172 A | 12/1982 | Lednicer ..................... 424/330 |
| 4,380,534 A | 4/1983 | Fukui et al. ................. 424/38 |
| 4,389,393 A | 6/1983 | Schor et al. ................. 424/19 |
| 4,421,736 A | 12/1983 | Walters ...................... 424/19 |
| 4,483,847 A | 11/1984 | Augart ........................ 424/22 |
| 4,533,562 A | 8/1985 | Ikegami et al. ............... 427/3 |
| 4,613,619 A | 9/1986 | Sleigh et al. ............... 514/546 |
| 4,708,874 A | 11/1987 | De Haan et al. ........... 424/470 |
| 4,797,410 A | 1/1989 | El-Fakahany .............. 514/356 |
| 4,801,458 A | 1/1989 | Hidaka et al. ............. 424/443 |
| 4,801,460 A | 1/1989 | Goertz et al. .............. 424/465 |
| 4,828,836 A | 5/1989 | Elger et al. ................ 424/419 |
| 4,834,984 A | 5/1989 | Goldie et al. .............. 424/465 |
| 4,834,985 A | 5/1989 | Elger et al. ................ 424/488 |
| 4,844,907 A | 7/1989 | Elger et al. ................ 424/465 |
| 4,844,909 A | 7/1989 | Goldie et al. .............. 424/480 |
| 4,861,598 A | 8/1989 | Oshlack ..................... 424/468 |
| 4,880,830 A | 11/1989 | Rhodes ...................... 424/470 |
| 4,894,234 A | 1/1990 | Sharma et al. ............. 424/440 |
| 4,917,899 A | 4/1990 | Geoghegan et al. ........ 424/461 |
| 4,925,675 A | 5/1990 | Giannini et al. ............ 424/469 |
| 4,935,246 A | 6/1990 | Ahrens ...................... 424/490 |
| 4,987,136 A | 1/1991 | Kreek et al. ................ 514/282 |
| 4,990,341 A | 2/1991 | Goldie et al. .............. 424/484 |
| 5,007,790 A | 4/1991 | Shell ......................... 424/451 |
| 5,023,089 A | 6/1991 | Sakamoto et al. .......... 424/502 |
| 5,026,560 A | 6/1991 | Makino et al. ............. 424/494 |
| 5,030,400 A | 7/1991 | Danielsen et al. .......... 264/101 |
| 5,071,646 A | 12/1991 | Malkowska et al. ........ 424/497 |
| 5,073,379 A | 12/1991 | Klimesch et al. ........... 424/467 |
| 5,126,145 A | 6/1992 | Evenstad et al. ........... 424/465 |
| 5,132,142 A | 7/1992 | Jones et al. ................. 427/196 |
| 5,133,974 A | 7/1992 | Paradissis et al. .......... 424/480 |
| 5,162,117 A | 11/1992 | Stupak et al. .............. 424/475 |
| 5,167,964 A | 12/1992 | Muhammad et al. ....... 424/482 |
| 5,169,645 A | 12/1992 | Shukla et al. .............. 424/499 |
| 5,178,868 A | 1/1993 | Malmqvist-Granlund et al. ........................... 424/490 |
| 5,196,203 A | 3/1993 | Boehm ...................... 424/469 |
| 5,202,128 A | 4/1993 | Morella et al. ............. 424/469 |

(Continued)

FOREIGN PATENT DOCUMENTS

CA          2131350          3/1995

(Continued)

OTHER PUBLICATIONS

CAPLUS Online Printout of Raffa et al (Caplus 1992: 120745, J. Pharmacol. Exp. Ther. 1992, 260 (1), 275-85).*

(Continued)

*Primary Examiner*—Samuel Barts
(74) *Attorney, Agent, or Firm*—Davidson, Davidson & Kappel, LLC

(57) ABSTRACT

A controlled release preparation for oral administration contains tramadol, or a pharmaceutically acceptable salt thereof, as active ingredient.

17 Claims, 2 Drawing Sheets

U.S. PATENT DOCUMENTS

| | | | |
|---|---|---|---|
| 5,204,119 A | 4/1993 | Shiobara et al. ............. | 424/489 |
| 5,266,331 A | 11/1993 | Oshlack et al. ............. | 424/468 |
| 5,271,934 A | 12/1993 | Goldberg et al. ........... | 424/401 |
| 5,273,760 A | 12/1993 | Oshlack et al. ............. | 424/480 |
| 5,286,493 A | 2/1994 | Oshlack et al. ............. | 424/468 |
| 5,292,461 A | 3/1994 | Juch et al. .................... | 264/37 |
| 5,300,300 A | 4/1994 | Egidio et al. ............... | 424/456 |
| 5,321,012 A | 6/1994 | Mayer et al. ................. | 514/25 |
| 5,330,766 A | 7/1994 | Morella et al. ............. | 424/490 |
| 5,395,626 A | 3/1995 | Kotwal et al. ............... | 424/472 |
| 5,403,593 A | 4/1995 | Royce ......................... | 424/489 |
| 5,453,283 A | 9/1995 | Münch et al. ............... | 424/489 |
| 5,456,921 A | 10/1995 | Mateescu et al. | |
| 5,468,744 A | 11/1995 | Raffa et al. ................. | 514/282 |
| 5,472,710 A | 12/1995 | Klokkers-Bethke et al. | 424/468 |
| 5,472,712 A | 12/1995 | Oshlack et al. ............. | 424/480 |
| 5,478,577 A | 12/1995 | Sackler et al. .............. | 424/489 |
| 5,521,178 A | 5/1996 | Nickel et al. ............... | 514/23.2 |
| 5,549,912 A | 8/1996 | Oshlack et al. ............. | 424/468 |
| 5,580,578 A | 12/1996 | Oshlack et al. ............. | 424/468 |
| 5,591,452 A * | 1/1997 | Miller et al. ................ | 424/468 |
| 5,603,956 A | 2/1997 | Mateescu et al. | |
| 5,616,343 A | 4/1997 | Cartilier et al. | |
| 5,639,476 A | 6/1997 | Oshlack et al. ............. | 424/468 |
| 5,849,240 A | 12/1998 | Miller et al. ................ | 264/460 |
| 5,885,615 A | 3/1999 | Chouinard et al. | |
| 5,891,471 A | 4/1999 | Miller et al. ................ | 424/468 |
| 5,958,452 A | 9/1999 | Oshlack et al. ............. | 424/457 |
| 5,958,459 A | 9/1999 | Chasin et al. ............... | 424/490 |
| 5,965,161 A | 10/1999 | Oshlack et al. ............. | 424/457 |
| 5,965,163 A | 10/1999 | Miller et al. ................ | 424/468 |
| 5,968,551 A | 10/1999 | Oshlack et al. ............. | 424/456 |
| 6,068,855 A | 5/2000 | Leslie et al. ................ | 424/468 |
| 6,103,261 A | 8/2000 | Chasin et al. ............... | 424/459 |
| 6,143,322 A | 11/2000 | Sackler et al. .............. | 424/459 |
| 6,143,353 A | 11/2000 | Oshlack et al. ............. | 427/221 |
| 6,162,467 A | 12/2000 | Miller et al. ................ | 424/468 |
| 6,254,887 B1 * | 7/2001 | Miller et al. ................ | 424/468 |
| 6,261,599 B1 | 7/2001 | Oshlack et al. ............. | 424/457 |
| 6,294,195 B1 | 9/2001 | Oshlack et al. ............. | 424/457 |
| 6,306,438 B1 | 10/2001 | Oshlack et al. ............. | 424/468 |
| 6,326,027 B1 | 12/2001 | Miller et al. ................ | 424/468 |
| 6,335,033 B1 | 1/2002 | Oshlack et al. ............. | 424/457 |
| 6,338,859 B1 | 1/2002 | Leroux et al. | |
| 6,399,096 B1 | 6/2002 | Miller et al. ................ | 424/464 |
| 6,419,957 B1 | 7/2002 | Lenaerts et al. | |
| 6,607,748 B1 | 8/2003 | Lenaerts et al. | |
| 6,645,527 B1 | 11/2003 | Oshlack et al. ............. | 424/468 |
| 6,743,442 B1 | 6/2004 | Oshlack et al. ............. | 424/456 |
| 2003/0124184 A1 | 7/2003 | Mezaache et al. .......... | 424/465 |

FOREIGN PATENT DOCUMENTS

| | | |
|---|---|---|
| DE | 3602370 | 8/1987 |
| DE | 3623193 | 1/1988 |
| DE | 4329794 | 3/1995 |
| DE | 4329794 A1 | 3/1995 |
| EP | 0032004 | 12/1980 |
| EP | 0043254 | 1/1982 |
| EP | 0097523 | 8/1983 |
| EP | 0043254 | 5/1984 |
| EP | 0108218 | 5/1984 |
| EP | 0108218 A2 | 5/1984 |
| EP | 0147780 | 12/1984 |
| EP | 0147780 | 7/1985 |
| EP | 0152379 | 8/1985 |
| EP | 0214735 | 7/1986 |
| EP | 0189861 | 8/1986 |
| EP | 0248548 | 5/1987 |
| EP | 0249347 | 5/1987 |
| EP | 0251459 | 5/1987 |
| EP | 0253104 | 6/1987 |
| EP | 0254978 | 2/1988 |
| EP | 0256127 | 2/1988 |
| EP | 0256127 B1 | 2/1988 |
| EP | 0267702 | 5/1988 |
| EP | 0271193 | 6/1988 |
| EP | 0271193 A2 | 6/1988 |
| EP | 0300897 | 7/1988 |
| EP | 0295212 | 12/1988 |
| EP | 0327295 | 8/1989 |
| EP | 0338383 | 10/1989 |
| EP | 0068450 | 1/1990 |
| EP | 0351580 | 1/1990 |
| EP | 0377518 | 1/1990 |
| EP | 0361680 | 4/1990 |
| EP | 0361910 | 4/1990 |
| EP | 0368247 | 5/1990 |
| EP | 0377517 | 7/1990 |
| EP | 0377518 | 7/1990 |
| EP | 0298355 | 11/1990 |
| EP | 0415693 | 3/1991 |
| EP | 0430287 B1 | 6/1991 |
| EP | 0463833 | 6/1991 |
| EP | 0241615 | 9/1991 |
| EP | 0452145 | 10/1991 |
| EP | 0531611 | 4/1992 |
| EP | 0535841 | 9/1992 |
| EP | 0526862 | 2/1993 |
| EP | 0533297 | 3/1993 |
| EP | 0534628 | 3/1993 |
| EP | 0546676 | 6/1993 |
| EP | 0595311 | 5/1994 |
| EP | 0361910 | 6/1994 |
| EP | 0636370 | 2/1995 |
| EP | 0642788 | 3/1995 |
| EP | 0609961 | 8/1995 |
| EP | 0205282 | 9/1995 |
| EP | 0624366 | 5/1996 |
| FR | 2642420 | 3/1990 |
| GB | 997399 | 4/1964 |
| GB | 1405088 | 6/1971 |
| GB | 1513166 | 6/1978 |
| GB | 2111386 | 12/1982 |
| GB | 2117239 | 3/1983 |
| GB | 2053681 | 4/1984 |
| GB | 2196848 | 5/1988 |
| GB | 2246514 | 2/1992 |
| GB | 2287880 | 10/1995 |
| JP | 5492631 | 7/1979 |
| JP | 4217925 | 8/1992 |
| JP | 2568202 | 12/1996 |
| WO | WO 9119484 | 12/1991 |
| WO | WO 9119485 | 12/1991 |
| WO | 9201446 | 2/1992 |
| WO | WO 9201446 | 2/1992 |
| WO | WO 9202209 | 2/1992 |
| WO | WO 9205774 | 4/1992 |
| WO | WO 9206679 | 4/1992 |
| WO | WO 9300076 | 1/1993 |
| WO | WO 9304675 | 3/1993 |
| WO | WO 9307859 | 4/1993 |
| WO | WO 9307861 | 4/1993 |
| WO | WO 9317667 | 9/1993 |
| WO | WO 9318753 | 9/1993 |
| WO | WO 9324110 | 12/1993 |
| WO | WO 9403160 | 2/1994 |
| WO | WO 9403161 | 2/1994 |
| WO | WO 9405262 | 3/1994 |
| WO | WO 9422431 | 10/1994 |
| WO | WO 9423700 | 10/1994 |
| WO | WO 9514460 | 6/1995 |
| WO | 03072025 | 9/2003 |
| WO | 03072089 | 9/2003 |
| WO | 04000197 | 12/2003 |

WO 04080447 9/2004

OTHER PUBLICATIONS

Von K. Flick, E. Frankus and E. Friderichs—Tramadol, 107-113, *Untersuchungen zur chemischen Struktur und analgetischen Wirkung von phenylsubstituierten Aminomethylcyclohexanolen*, Arzneimittel-Forschung, Drug Res. 28 (I), Heft 1a, and English translation.

Kuschinsky et al., *Kurzes Lehrbuch der Pharmakologie end Toxikologie*, Georg Theime Verlag Stuttgart, New York 1987, p. 270-273.

Von E. Frankus, E. Friderichs, S.M. Kin und G. Osterioh, *Über die Isomerentrennung, Strukturaufklärung und pharmakologische Charakterisierung von 1-(m-Methoxyphenyl)-2-(dimethylaminomethyl)-cyclohexan-1-ol*, Arzneim-Forsch. Drug Res. (I), Heft 1a (1978), 144-121 and English translation.

Rote Liste 1992, Entry No. 05020.

Derwent WPI C92-138727 Abstract JP 04/217 925 of Aug. 7, 1992.

Herbert P Fiedler: Lexicon der Hilfsstoffe, 34d Ed., 1989, p. 272-273.

Sucker et al., (Eds.), Pharmazeutische Technologie, Stuttgart, 1979, p. 497-498.

Von W. Vogel, H. Burchardi, K. Sihler und L. Valic, *Über die Wirkung von Tramadol auf Atmung und Kreislauf*, Arzneimittel-Forschung, Drug. Res. 28(1), Heft 1a (1978), pp. 183-186 and English translation.

Von W. Lintz, S. Erlacin, E. Frankus and H. Uragg, *Metabolismus von Tramadol bei Mensch and Tier*, Arzneimittel-Forschung, Drug Res. 31 (II), No. 11 (1981), pp. 1932-1943 and English translation.

Von F. Lagler, F. Helm, V. Etzel und H. Kiel, *Toxikologische Untersuchungen mit Tramadol, einem neuen Analgetikum*, Arzneimittel-Forschung, Drug Res. 28(I), Heft 1a (1978), pp. 164-172 and English translation.

Von G. Osterloh, E. Friderichs*, F. Felgenheuer*, W.A. Gunzler, Z. Henmi, T. Kitano, M. Nakamura, H. Hayashi und I. Ishii**, *Allgemeine pharmakologische Untersuchungen mit Tramadol, einem stark wirkenden Analgetikum*, Arzneimittel-Forschung, Drug Res. 28(I), Heft 1a (1978), pp. 135-151 and English translation.

Von E. Friderichs, F. Felgenhauer, P. Jongschaap und G. Osterloh, *Pharmakologische Untersuchungen zur Analgesie, Abhängigkeits- und Toleranzentwicklung von Tramadol, einem stark wirkenden Analgetikum*, Arzneimittel-Forschung Drug Res. 28(I), Heft 1a, pp. 122-134 and English translation.

L. Collart, C. Luthy, C. Favario-Constantin, P. Dayer, *Dualite de l'effet analgesique du tramadol chez l'homme*, Schwiz Med. Wochenschr. 1993:123:, pp, 2241-2243 and English translation.

E. Beubler, *Medikamentose Schmerztherapie: Kriterien, Möglichkeiten, Risken*, Therapiewoche Österreich 7,2 (1992), pp. 90-96 and English translation.

Kaiko, et al., *A Single-dose Study of the Effect of Food Ingestion and Timing of Dose Administration on the Pharmacokinetic Profile of 30mg Sustained-release Morphine Sulfate Tablets*, Current Therapeutic Research, pp. 869-878, vol. 47, No. 5, May 1990.

Kaiko, et al., *Controlled-release Morphine Bioavailability (MS Contin™ Tablets) in the Presence and Absence of Food*. The Hospice Journal, pp. 17-30, vol. 6(4) 1990.

Gourlay, et al., *the Reproducibility of Bioavailability of Oral Morphine from Solution under Fed and Fasted Conditions*, Journal of Pain and Symptom Management, vol. 6, No. 7, Oct. 1991, pp. 431-436.

Gourlay, et al., *Influence of a High-fat Meal on the Absorption of Morphine from Oral Solutions*, Clin. Pharmacol. Ther., Oct. 1989, pp. 403-468.

Physicians Desk Reference 1994, 48th Edition, pp. 1821-1824.

Advertisement: Roxanol SR., 1988 Roxane Labs, Inc.

R. Kaiko and T. Hunt, *Comparison of the Pharmacokinetic Profiles of Two Oral Controlled-Release Morphine Formulations in Healthy Young Adults*, Clin. Thera. vol. 13, No. 4, 1991, pp. 484-488.

Thomsen, L. Juul, *Prolonged Release Matrix Pellets Prepared by Melt Pelletization. Part IV: Drug Content, Drug Particle Size, and Binder Composition*, Pharmaceutical Technology Europa, (Oct. 1994), pp. 19-22.

McTaggart, C.M., et al., *The Evaluation of Formulation and Processing Conditions of a Melt Granulation Process*, Int. J. Pharm., vol. 19, No. 2, issued 1984, pp. 139-148.

El-Shanawany, S., *Sustained Release of Nitrofurantoin From Inert Wax Matrixes*, J. Controlled Release, vol. 26, No. 1, issued 1993, pp. 11-19.

S. Bloomfield, et al., *Analgesic Efficacy and Potency of Two Oral Controlled-Release Morphine Preparations*, Clin. Pharmacol. Ther., vol. 53, No. 4, 1993, pp. 469-478.

Advertisement, MS Contin™ 1986, 1987 The Purdue Frederick Company.

P. Flanders, et al., *The Control of Drug Releases From Conventional Melt Granulation Matrices*, Drug Development and Industrial Pharmacy, vol. 13, No. 6, (1987), pp. 1001-1022.

T. Schaefer, et al., *Melt granulation in a laboratory scale high shear mixer*, Drug Development and Industrial Pharmacy, vol. 16, No. 8, (1990), pp. 1249-1277.

Thompson, L. Juul et al., Schaefer, T., et al., *Prolonged Release Matrix Pellets Prepared by Melt Pelletization, I. Process Variables*, Drug Development and Industrial Pharmacy, vol. 19, No. 15, pp. 1867-1887.

Thomsen, L. Juul, et al., *Prolonged Release Matrix Pellets Prepared by Melt Pelletization, Part IV. Drug Content, Drug Particle Size, and Binder Composition*, Pharmaceutical Technology Europe, (Oct. 1994), pp. 19-24.

Thomsen, L. Juul, *Utilizing melt pelletization technique for the preparation of prolonged released products, Pelletization*, (material elaborated by Assistant Prof. Lars Juul Thomsen, Dept. of Pharmaceutics, Royal Danish School of Pharmacy for the DIE course "Pelletization Technology", Nov. 1992, Sectons I to VI.

SK Baveja et al., Int. J. Pharmaceutics, 41, (1988) p. 55-62.

Formulating for Controlled Release with METHOCEL® Premium Cellulose Ethers. The Dow Chemical Company, 1989.

M S Vasquez et al., Drug Dev. & Ind. Pharmacy, 18 (11&12), p. 1355-1378 (1992).

L W S Cheong et al., Pharm. Res 9 (11) p. 1510-1514 (1992).

Pharmazeutische Stoffliste 6th Ed., 1985 p. 196.

Rote Liste 1993 Nos. 05001 & 05008.

Derwent Abstract 92:64751.

Haltbarkeits-Herstellungdaten deutscher Arzneimittel p. 486.

Goodman and Gilmans, 8th Ed., 1990: p. 497.

Hunt, et al., Clin. Ther. vol. 13, No. 4, 1991, pp. 482-488.

Lee et al. Drugs 46(2), 1993, pp. 313-340.

The Merck Index 11th Ed., 1989.

Pharmazeutische Stoffliste 10. Auflage, p. 193, Nov. 1994.
Rote Liste 1992 Entry 05007.
PIL (Product Information Leaflet) about MST CONTINUS® tablets.
Graph of dissolution rates claimed in the patent EP 0 624 366.
The Physician's Desk Reference, 1994. Monograph on MS CONTIN® (MST CONTINUS® ) tablets.
Copy from USPXXII with Supplements of Extended Release monographs.
METHOCEL, Colorcon Technical Information.
DA Alderman, Int. J. Pharm. Tech. and Prod. Mfr., 5(3) p. 1-9, 1984.
HE Huber et al., J. Pharm. Sci. 55 (9) Sep. 1966, p. 974-976.
Lin SY et al., Current Therapeutic Research 52(3), p. 486-492, Sep. 1992.
Handbook of Pharmaceutical Excipients, p. 138-140, 1986.
Aqualon Technical Information Bulletin VC-585, 1991.
P Colombo, Advanced Drug Delivery Reviews, 11 (1993) p. 37-57.
KV Ranga Rao et al., Int. J. Pharmaceutics, 48 (1988) p. 1-13.
JE Hogan, Drug Dev. & Ind. Pharmacy, 15 (6 & 7), p. 975-999 (1989).
JL Ford et al., Int. J. Pharmaceutics, 24 (1985) p. 327-338.
PB Daly et al. Int. J. Pharmaceutics, 18 (1984) p. 201-205.
H Lapidus et al., J. Pharm. Sci., 55(8), Aug. 1966, p. 840-843.
H Lapidus et al., J. Pharm. Sci., 57(8), Aug. 1968, p. 1292-1301.
Abstract of JP 54/092631, published Jul. 23, 1979.
Stanislaw Janicki and Zdzisiaw Jedras, *Slow-Release Microballs: Method of Preparation*, Acta. Pharm. Technol. 33(3) (1987), pp. 154-155.
B. Elsing and G. Blaschke, *Achiral and chiral high-performance liquid chromatographic determination of tramadol and its major metabolites in urine after oral administration of racemic tramadol*, Journal of Chromatography, 612 (1993), pp. 223-230.
C.H.W. Koks, A.P.E. Vielvoye-Kerkmeer, and J.H. Beijnen, *Tramadol (Tramal)*, Pharm. Weekbl. 1993: 128(4): 1298-1300.
W. Lintz and H. Uragg, *Quantitative Determination of Tramadol in Human Serum by Gas Chromatography—Mass Spectrometry*, Journal of Chromatography, 341 (1985), pp. 65-79.
Pharm. Res. 1992; Supp. 9:308, *Tramadol*, PPDM's 8207 and 8206.
J.M. Aiache and J. Hirtz, *Biopharmaceutics—Absolute Bioavailability of Tramal Suppositories*, Third European Congress of Biopharmaceutics and Pharmacokinetics Proceedings—vol. 1, p. 311.
W. Lintz, H. Barth, G. Osterloh, and E. Schmid-Bothelt, *Bioavailability of Enteral Formulations 1st Communication: Capsules*, Arzeimittal-Forschung, Drug Res. 36 (II) Nr. 8 (1986), pp. 1278-1283.
Clinical Pharm. & Ther. vol. 53, No. 2, *American Society for Clinical Pharmacology and Therapeutics*, P111-67, P111-68 and P111-69.
Jean-Marie Besson and Michael D. Vickers, *Tramadol Analgesia Synergy in Research and Therapy*, Drugs 47 (Suppl. 1):1-2, 1994, Adis International Limited.
Pierre Dayer, Laurence Collart and Jules Desmeules, *The Pharmacology of Tramadol*, Drugs 47 (Suppl. 1):3-7, 1994, Adis International Limited.
Abraham Sunshine, *New Clinical Experience with Tramadol*, Drugs 47(Supp. 1) 8-18, 1994, Adis International Limited.
Klaus A. Lehmann, *Tramadol for the Management of Acute Pain*, Drugs 47 (Supp. 1): 19-32, 1994, Adis International Limited.
Keith Budd, *Chronic Pain—Challenge and Response*, Drugs 47 (Suppl. 1):39-43, 1994, Adis International Limited.
Jordi Cami, Xavier Lamas and Magi Farre, *Acute Effects of Tramadol in Methadone-Maintained Volunteers*, Drugs 47 (Supp. 1):39-43, 1994, Adis International Limited.
C.H.W. Koks, A.P.E. Vielvoye-Kerkmeer, and J.H. Beijnen, *Tramadol (Tramal)*.
C. Rhoda Lee, Donna Mc Tavish and Eugene M. Surkin, "Tramadol, A Preliminary Review of its Pharmacodynamic Properties, and Therapeutic Potential in Acute and Chronic Pain States", Drugs 46(2):313-340, 1993, Adis International Limited.
Valerie Kayser, Jean-Marie Besson, and Gisele Gilbaud, *Evidence for a noradrenergic component in the antinociceptive effect of the analgesic agent tramadol in an animal model of clinical pain, the arthritic rat*, European Journal of Pharmacology, 224(1992), pp. 83-88.
Kenzie L. Preston, Donald R. Jasinksi and Margaret Testa, *Abuse potential and pharmacological comparison of tramadol and morphine*, Drug and Alcohol Dependence, 27 (1991), pp. 7-17.
Valerie Kayser, Jean-Marie Besson and Gisele Guilbaud, *Effects of the analgesic agent tramadol in normal and arthritic rats: comparison with the effects of different opioids, including tolerance and cross-tolerance to morphine*, European Journal of Pharmacology, 195 (1991) 37-45.
T. Murano, H. Yamamoto, N. Endo, Y. Kudo, N. Okada, Y. Masuda, and I. Yano,*Studies of Dependence on Tramadol in Rats*, Arzneimittel-Forschung, Drug Res. 28(I) Heft 1a (1978).
T. Yanagita, *Drug Dependence Potential of 1-(m-Methoxyphenil)-2-(dimethylaminomethyl)-cyclohesan-1-ol Hydrochloride (Tramadol) Tested in Monkeys*, Arzneimittel-Forschung Drug Res. 28(1), Heft 1a (1978), pp. 158-163.
Abraham Sunshine, MD, Nancy Z. Olson, MPS, Itic Zighelboim, MD. Ana DeCastro, RN, and Frederick L. Minn, MD, PhD, *Analgesic oral efficacy of tramadol hydrochloride in postoperative pain*, Clin. Pharmacol. Ter. (Jun. 1992), pp. 740-146.
Translation of Japanese Patent Publication No. 43 (1968) 20006, Detailed Description of the Invention.
M. Ahmend and R.P. Enever, *Formulation and Evaluation of Sustained Release Paracetamol Tablet*, Journal of Clinical and Hospital Pharmacy (1981) 6, pp. 27-38.
M.D. Vickers, D. O'Flaherty, S.M. Szekely, M. Read and J. Yoshizumi, *Tramadol: pain relief by an opioid without depression of respiration*, Anaesthesia, 1992, vol. 47, pp. 291-296.
G.M. Hanna, C.A. Lau-Cam and W.M. Plank, *Direct determination of the enantiomeric purity of tramadol hydrochloride by proton nuclear resonance (1H NMR spectroscopy with chiral lanthanide shifr reacgent*. Pharamzie 44 (1989), H. 5, pp. 321-325.
Martindale, The Extra Pharmacopoeia, 28th Ed., 198, 6263-c, Tramadol hydrochloride, pp. 1029-1030.
Anderson, H.O. & Christensen, H., *In vitro and in vivo investigations of a new timed-release dosage form of*

*propoxyphene hydrochloride*, Dansk tidsskrift for farmaci, vol. 43, 1969, pp. 117-126.

Schmidhammer, Helmut, *Synthesis and Biological Evaluation of 14-Alkoxymorphinans*, Helvetica Chimica Acta, vol. 72, 1989, pp. 1233-1239.

Schmidhammer, Helmut, *Synthesis, Structure Elucidation, and Pharmacological Evaluation of 5-Methyloxymorphone*, Helvetica Chimica Acta, vol. 71, 1988, pp. 1801-1804.

Schmidhammer, Helmut, *Synthesis and Biological Evaluation of 14-Alkoxymorphinans*, J. Med Chem, (1990) vol. 33, No. 4, pp. 1200-1206.

ROTE LISTE® Service GmbH, Rote Liste 1998, Section 05.

S.J. Carter and R. Woodford, "Long-Acting Oral Medicaments", Pharmacy Digest (1961) pp. 183-189.

Remington's Pharmaceutical Sciences, 1980, p. 1598.

Thomsen, L. Juul, et al., *Prolonged Release Matrix Pellets Prepared by Melt Pelletization II. Hydrophobic Substances as Meltable Binders*, Drug Development and Industrial Pharmacy, vol. 20, No. 7, (1984), pp. 1179-1197.

\* cited by examiner

CONTROLLED RELEASE TRAMADOL TRAMADOL FORMULATION

This application is a continuation of U.S. patent application Ser. No. 08/677,798, filed Jul. 10, 1996; now U.S. Pat. No. 6,254,887 which is a continuation of U.S. patent application Ser. No. 08/241,129, filed May 10, 1994 (now U.S. Pat. No. 5,591,452).

The present invention relates to a controlled release preparation for oral administration, to processes for its preparation and to its medical use. In particular, the invention relates to a controlled release preparation comprising tramadol or a pharmaceutically acceptable salt thereof.

Tramadol, which has the chemical name (±)-trans-2-[(dimethylamino)methyl]-1-(3-methoxyphenyl) cyclohexanol, is an orally active opioid analgesic. Conventional release preparations in the form of capsules, drops and suppositories containing tramadol, or more particularly its hydrochloride salt, have been commercially available for many years for use in the treatment of moderate to severe pain; Such preparations, however, do not provide a controlled release of the tramadol. Moreover, despite tramadol's long-standing use, controlled release preparations for oral administration containing tramadol as active ingredient have not even previously been described in the literature.

It is an object of the present invention to provide an oral controlled release tramadol preparation suitable for at least twelve-hourly (e.g. up to twenty-four hourly) administration for the treatment of pain.

The present invention therefore provides a controlled release preparation comprising tramadol or a pharmaceutically acceptable salt thereof for oral administration.

Suitable pharmaceutically acceptable salts of tramadol for use according to the present invention are those conventionally known in the art such as pharmaceutically acceptable acid addition salts. The hydrochloride salt is particularly preferred.

A controlled release preparation according to the present invention is one that achieves slow release of a drug over an extended period of time, thereby extending the duration of drug action over that achieved by conventional delivery. Preferably such a preparation maintains a drug concentration in the blood within the therapeutic range for 12 hours or more.

The present inventors have found that in order to allow for controlled release tramadol over at least a twelve hour-period following oral administration, the in vitro release rate preferably corresponds to the following % rate of tramadol released:

TABLE 1

| TIME (H) | % RELEASED |
| --- | --- |
| 1 | 0–50 |
| 2 | 0–75 |
| 4 | 3–95 |
| 8 | 10–100 |
| 12 | 20–100 |
| 16 | 30–100 |
| 24 | 50–100 |
| 36 | >80 |

Another preferred preparation especially suited for twice-a-day dosing has an in vitro release rate corresponding to the following % rate of tramadol released:

TABLE 2

| TIME (H) | % RELEASED |
| --- | --- |
| 1 | 20–50 |
| 2 | 40–75 |
| 4 | 60–95 |
| 8 | 80–100 |
| 12 | 90–100 |

Yet another preferred preparation particularly suited for once-a-day dosing has an in-vitro release rate corresponding to the following % rate of tramadol released:

TABLE 3

| TIME (H) | % RELEASED |
| --- | --- |
| 1 | 0–50 |
| 2 | 0–75 |
| 4 | 10–95 |
| 8 | 35–100 |
| 12 | 55–100 |
| 16 | 70–100 |
| 24 | >90 |

A still further preferred preparation in accordance with the invention also particularly suited for once-a-day dosing has an in vitro release rate corresponding to the following % rate of tramadol released.

TABLE 4

| TIME (H) | % RELEASED |
| --- | --- |
| 1 | 0–30 |
| 2 | 0–40 |
| 4 | 3–55 |
| 8 | 10–65 |
| 12 | 20–75 |
| 16 | 30–88 |
| 24 | 50–100 |
| 36 | >80 |

More preferably a preparation for once-a-day dosing has an in vitro release rate substantially as follows:

| TIME (H) | % TRAMADOL RELEASED |
| --- | --- |
| 1 | 15–25 |
| 2 | 25–35 |
| 4 | 30–45 |
| 8 | 40–60 |
| 12 | 55–70 |
| 16 | 60–75 |

Another preferred dissolution rate in vitro upon release of the controlled release preparation twice daily according to the invention, is between 5 and 50% (by weight) tramadol released after 1 hour, between 10 and 75% (by weight) tramadol released after 2 hours, between 20 and 95% (by weight) tramadol released after 4 hours, between 40 and 100% (by weight) tramadol released after 8 hours, more than 50% (by weight) tramadol released after 12 hours, more than 70% (by weight) released after 18 hours and more than 80% (by weight) tramadol released after 24 hours.

Furthermore, it is preferred in the case of a controlled release preparation for administration twice daily that after 8 hours following oral administration between 70 and 95% (by weight) tramadol is absorbed in vivo, between 77 and 97% (by weight) tramadol is absorbed after 10 hours and between 80 and 100% (by weight) tramadol is absorbed after 12 hours.

A formulation in accordance with the invention suitable for twice-a-day dosing may have a tmax of 1.5 to 8 hours, preferably 2 to 7 hours, and a $W_{50}$ value in the range 7 to 16 hours.

A formulation in accordance with the invention suitable for once-a-day dosing may have a tmax in the range of 3 to 6 hours, preferably 4 to 5 hours and a $W_{50}$ value in the range of 10 to 33 hours.

The $W_{50}$ parameter defines the width of the plasma profile at 50% Cmax, i.e. the duration over which the plasma concentrations are equal to or greater than 50% of the peak concentration. The parameter is determined by linear interpolation of the observed data and represents the difference in time between the first (or only) upslope crossing and the last (or only) downslope crossing in the plasma profile.

The in vitro release rates mentioned herein are, except where otherwise specified, those obtained by measurement using the Ph. Eur. Paddle Method at 100 rpm in 900 ml 0.1 N hydrochloric acid at 37° C. and using UV detection at 270 nm.

The in viva absorption rate is determined from measurement of plasma concentration against time using the deconvolution techniqiue. A conventional release tramadol drop preparation (Tramal (trade mark), Grunenthal) was used as the weighting-function and the elimination half life of tramadol was taken as 7.8 hours.

The controlled release preparation according to the invention preferably contains an analgesically effective amount of tramadol or a pharmaceutically acceptable salt thereof, conveniently in the range of from 50 to 800 mg, especially 100, 200, 300, 400 to 600 mg (calculated as tramadol hydrochloride) per dosage unit.

The controlled release preparation according to the invention may be presented, for example, as granules, spheroids, pellets, multiparticulates, capsules, tablets, sachets, controlled release suspensions, or in any other suitable dosage form incorporating such granules, spheroids, pellets or multiparticulates.

The active ingredient in the preparation according to the invention may suitably be incorporated in a matrix. This may be any matrix that affords controlled release tramadol over at least a twelve hour period and preferably that affords in-vitro dissolution rates and in vivo absorption rates of tramadol within the ranges specified above. Preferably the matrix is a controlled release matrix. Alternatively, normal release matrices having a coating which provides for controlled release of the active ingredient may be used.

Suitable materials for inclusion in a controlled release matrix include (a) Hydrophillic or hydrophobic polymers, such as gums, cellulose ethers, acrylic resins and protein derived materials. Of these polymers, the cellulose ethers, especially alkylcelluloses are preferred. The preparation may conveniently contain between 1% and 80% (by weight) of one or more hydrophillic or hydrophobic polymers.

(b) Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes. Hydrocarbons having a melting point of between 25 and 90° C. are preferred. Of these long chain hydrocarbon materials, fatty (aliphatic) alcohols are preferred. The preparation may conveniently contain up to 60% (by weight) of at least one digestible, long chain hydrocarbon.

(c) Polyalkylene glycols. The preparation may suitably contain up to 60% (by weight) of one or more polyalkylene glycols.

One particularly suitable controlled release matrix comprises one or more alkylcelluloses and one or more $C_{12}$–$C_{36}$ aliphatic alcohols. The alkylcellulose is preferably $C_1$–$C_6$ alkyl cellulose, especially ethyl cellulose. The controlled release preparation according to the invention preferably contains from 1 to 20% (by weight), especially from 2 to 15% (by weight) of one or more alkylcelluloses.

The aliphatic alcohol may conveniently be lauryl alcohol, myristyl alcohol or stearyl alcohol but is preferably cetyl alcohol or more preferably cetostearyl alcohol. The controlled release preparation suitably contains from 5 to 30% (by weight) of aliphatic alcohol, especially from 10 to 25% (by weight) of aliphatic alcohol.

Optionally the controlled release matrix may also contain other pharmaceutically acceptable ingredients which are conventional in the pharmaceutical art such as diluents, lubricants, binders, granulating aids, colourants, flavourants, surfactants, pH adjusters, anti-adherents and glidants, e.g. dibutyl sebacate, ammonium hydroxide, oleic acid and colloidal silica.

The controlled release preparation according to the invention may conveniently be film coated using any film coating material conventional in the pharmaceutical art. Preferably an aqueous film coating is used.

Alternatively, the controlled release preparation according to the invention may comprise a normal release matrix having a controlled release coating. Preferably the preparation comprises film coated spheroids containing the active ingredient and a spheronising agent.

The spheronising agent may be any suitable pharmaceutically acceptable material which may be spheronised together with the active ingredient to form spheroids. A preferred spheronising agent is microcrystalline cellulose. The microcrystalline cellulose used may suitably be, for example, Avicel PII 101 or Avicel PII 102 (Trade Marks, FMC Corporation).

Optionally the spheroids may contain other pharmaceutically acceptable ingredients conventional in the pharmaceutical art such as binders, bulking agents and colourants. Suitable binders include water soluble polymers, water soluble hydroxyalkyl celluloses such as hydroxypropylcellulose or water insoluble polymers (which may also contribute controlled release properties) such as acrylic polymers or copolymers for example ethylcellulose. Suitable bulking agents include lactose.

The spheroids are coated with a material which permits release of the active ingredient at a controlled rate in an aqueous medium. Suitable controlled release coating materials include water insoluble waxes and polymers such as polymethacrylates (for example Eudragit polymers, Trade Mark) or water insoluble celluloses, particularly ethylcellulose. Optionally, water soluble polymers such as polyvinylpyrrolidone or water soluble celluloses such as hydroxypropylmethylcellulose or hydroxypropylcellulose may be included. Optionally other water soluble agents such as polysorbate 80 may be added.

Alternatively the drug may be coated onto inert non-pareil beads and the drug loaded beads coated with a material which permits control of the release of the active ingredient into the aqueous medium.

In a further aspect the present invention provides a process for preparing a controlled release preparation according to the present invention comprising incorporating tramadol or a pharmaceutically acceptable salt thereof in a controlled release matrix, for example by (a) granulating a mixture comprising tramadol or a pharmaceutically acceptable salt thereof and one or more alkylcelluloses, (b) mixing the alkylcellulose containing granules with one or more $C_{12-36}$ aliphatic alcohols; and optionally (c) shaping and compressing the granules, and film coating, if desired; or (d) granulating a mixture comprising tramadol or a pharmaceutically acceptable salt thereof, lactose and one or more alkylcelluloses with one or more $C_{12-36}$ aliphatic alcohol; and, optionally, (e) shaping and compressing the granules, and film coating, if desired.

The controlled release preparation according to the invention may also be prepared in the form of film coated spheroids by (a) granulating the mixture comprising tramadol or a pharmaceutically acceptable salt thereof and a spheronising agent;

(b) extruding the granulated mixture to give an extrudate;

(c) spheronising the extrudate until spheroids are formed; and (d) coating the spheroids with a film coat.

One preferred form of unit dose form in accordance with the invention comprises a capsule filled with controlled release particles essentially comprising the active ingredient, a hydrophobic fusible carrier or diluent and optionally a hydrophillic release modifier. In particular, the controlled release particles are preferably prepared by a process which comprises forming a mixture of dry active ingredient and fusible release control materials followed by mechanically working the mixture in a high speed mixer with an energy input sufficient to melt or soften the fusible material whereby it forms particles with the active ingredient. The resultant particles, after cooling, are suitably sieved to give particles having a size range from 0.1 to 3.0 mm, preferably 0.25 to 2.0 mm. An example according to the invention is described below which is suitable for the commercial production of dosage units.

When using such a processing technique it has been found that, in order most readily to achieve the desired release characteristics (both in vivo and in vitro as discussed above) the composition to be processed should comprises two essential ingredients namely:

(a) tramadol or salt thereof; and (b) hydrophobic fusible carrier or diluent; optionally together with (c) a release control component comprising a water-soluble fusible material or a particulate soluble or insoluble organic or inorganic material.

We have found that the total amount of tramadol or pharmaceutically acceptable salt thereof in the composition may vary within wide limits, for example from 10 to 90% by weight thereof.

The hydrophobic fusible component (b) should be a hydrophobic material such as a natural or synthetic wax or oil, for example hydrogenated vegetable oil, hydrogenated castor oil, microcrystalline wax, Beeswax, Carnauba wax or glyceryl monostearate, and suitably has a melting point of from 35 to 140° C., preferably 45 to 110° C.

The release modifying component (c), when a water soluble fusible material, is conveniently a polyethylene glycol and, when a particulate material, is conveniently a pharmaceutically acceptable material such as dicalcium phosphate or lactose.

Another preferred process for the manufacture of a formulation in accordance with the invention comprises (a) mechanically working in a high-speed mixer, a mixture of tramadol or a pharmaceutically acceptable salt in particulate form and a particulate, hydrophobic fusible carrier or diluent having a melting point from 35 to 140° C. and optionally a release control component comprising a water soluble fusible material, or a particulate soluble or insoluble organic or inorganic material at a speed and energy input which allows the carrier or diluent to melt or soften, whereby it forms agglomerates, (b) breaking down the larger agglomerates to give controlled release seeds; and (c) continuing mechanically working with optionally a further addition of low percentage of the carrier or diluent.

(d) optionally repeating steps (c) and possibly (b) one or more times.

This process is capable of giving a high yield (over 80%) of particles in a desired size range, with a desired uniformity of release rate of tramadol or salt thereof.

The resulting particles may be sieved to eliminate any over-or undersized material then formed into the desired dosage units by for example, encapsulation into hard gelatin capsules containing the required dose of the active substance or by compression into tablets.

In this method in accordance with the invention preferaby all the tramadol or salt thereof is added in step (a) together with a major portion of the hydrophobic fusible release control material used. Preferably the amount of fusible release control material added in step (a) is between 10% and 90% w/w of the total amount of ingredients added in the entire manufacturing operation, more preferably between 20% and 70% w/w.

Stage (a) of the process may be carried out in conventional high speed mixers with a standard stainless steel interior, e.g. a Collette Vactron 75 or equivalent mixer. The mixture is processed until a bed temperature about 40° C. or above is achieved and the resulting mixture acquires a cohesive granular texture, with particle sizes ranging from about 1–3 mm to fine powder in the case of non-aggregated original material. Such material, in the case of the embodiments described below, has the appearance of agglomerates which upon cooling below 40° C. have structural integrity and resistance to crushing between the fingers. At this stage the agglomerates are of an irregular size, shape and appearance.

The agglomerates are preferably allowed to cool. The temperature to which it cools is not critical and a temperature in the range room temperature to 37° C. may be conveniently used.

The agglomerates are broken down by any suitable means, which will comminute oversize agglomerates and produce a mixture of powder and small particles preferably with a diameter under 2 mm. It is currently preferred to carry out the classification using a Jackson Crockatt granulator using a suitable sized mesh, or a Comil with an appropriate sized screen. We have found that if too small a mesh size is used in the aforementioned apparatus the agglomerates melting under the action of the beater or impeller will clog the mesh and prevent further throughput of mixture, thus reducing yield. A mesh size of 12 has been found adequate.

The classified material is returned to the high speed mixer and processing continued. It is believed that this leads to cementation of the finer particles into particles of uniform size range.

In one preferred form of the method of the invention processing of the classified materials is continued, until the hydrophobic fusible materials used begin to soften/melt and optionally additional hydrophobic fusible material is then added. Mixing is continued until the mixture has been transformed into particles of the desired predetermined size range.

In order to ensure uniform energy input into the ingredients in the high speed mixer it is preferred to supply at least part of the energy by means of microwave energy.

Energy may also be delivered through other means such as by a heating jacket or via the mixer impeller and chopper blades.

After the particles have been formed they are cooled or allowed to cool, and may then be sieved to remove any over or undersized material.

The resulting particles may be used to prepare dosage units in accordance with the invention in the form of e.g. tablets or capsules in manners known per se.

We have also found that particles containing tramadol or a salt thereof produced by a melt processing as described in application PCT/SE93/00225 and the process described and claimed in our prior unpublished UK application No. 9324045.5 filed on 23 Nov. 1993 as well as the process described herein are particularly useful for processing into the form of tablets.

We have found that by suitable selection of the materials used in forming the particles and in the tabletting and the proportions in which they are used, enables a significant degree of control in the ultimate dissolution and release rates of the tramadol or salt thereof from the compressed tablets.

Usually, to form a tablet in accordance with the invention, particles prepared as described above will be admixed with tabletting excipients e.g. one or more of the standard excipients such as diluents, lubricants, binding agents, flow aids, disintegrating agents, surface active agents or water soluble polymeric materials.

Suitable diluents are e.g. microcrystalline cellulose, lactose and dicalcium phosphate. Suitable lubricants are e.g. magnesium stearate and sodium stearyl fumarate. Suitable binding agents are e.g. hydroxypropyl methyl cellulose, polyvidone and methyl cellulose.

Suitable disintegrating agents are starch, sodium starch glycolate, crospovidone and croscarmalose sodium.

Suitable surface active are Poloxamer 188®, polysorbate 80 and sodium lauryl sulfate.

Suitable flow aids are talc colloidal anhydrous silica.

Suitable water soluble polymers are PEG with molecular weights in the range 1000 to 6000.

To produce tablets in accordance with the invention, particles produced in accordance with the invention may be mixed or blended with the desired excipient(s), if any, using conventional procedures, e.g. using a Y-Cone or bin-blender and the resulting mixture compressed according to conventional tabletting procedure using a suitable size tabletting mould. Tablets can be produced using conventional tabletting machines, and in the embodiments described below were produced on standard single punch F3 Manesty machine or Kilian RLE15 rotary tablet machine.

Generally speaking we find that even with such a highly water soluble active agent as tramadol or salt thereof tablets formed by compression according to standard methods give very low release rates of the active ingredient e.g. corresponding to release over a period of greater than 24 hours, say more than 36. We have found that the release profile can be adjusted in a number of ways. For instance a higher loading of the drug will be associated with increased release rates; the use of larger proportions of the water soluble fusible material in the particles or surface active agent in the tabletting formulation will also be associated with a higher release rate of the active ingredient. By controlling the relative amounts of these ingredients it is possible to adjust the release profile of the tramadol or salt thereof.

In order that the invention may be well understood the following examples are given by way of illustration only.

BRIEF DESCRIPTION OF THE DRAWINGS

The present invention is further illustrated with the accompanying drawings in which.

EXAMPLE 1

Figure 1:
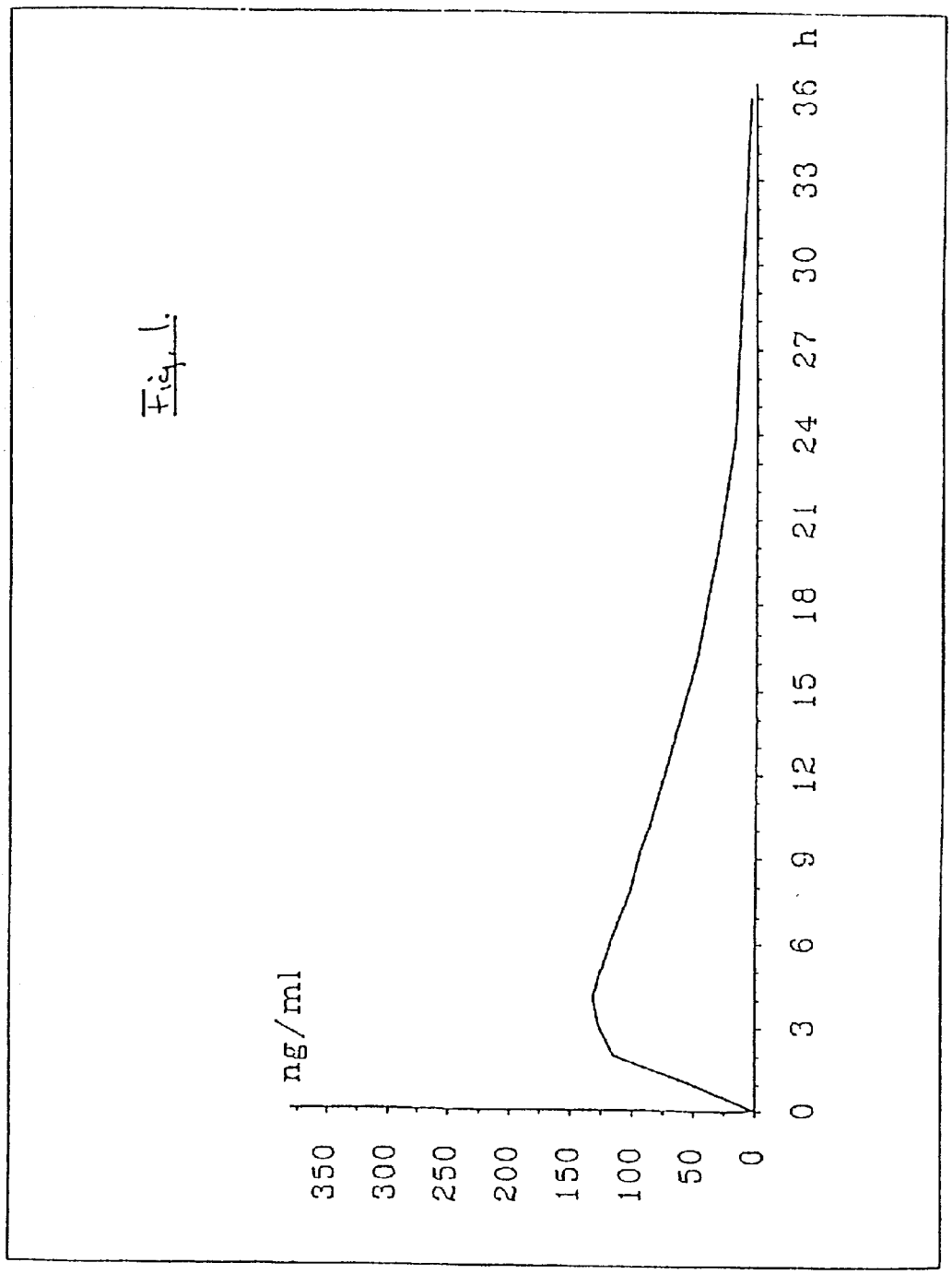
FIG. 1 is a graphical depiction of the serum levels of tramadol following administration of one tablet according to Example 2 in 12 healthy volunteers.

Tablets having the following formulation were prepared:

|  | mg/tablet |
|---|---|
| Tramadol Hydrochloride | 100 |
| Lactose Ph. Eur. | 68.0 |
| Ethylcellulose (Surelease ® 25% solids) | 15 |
| Purified Water Ph. Eur. | 13.3* |
| Cetostearyl Alcohol Ph. Eur. (Dehydag wax O) | 42.00 |
| Magnesium Stearate Ph. Eur. | 2.00 |
| Purified Talc Ph. Eur. | 3.00 |
|  | 230.00 |

*Removed during processing.

Tramadol hydrochloride (100 mg) and lactose (68 mg) were granulated, transferred to a fluid bed granulator and sprayed with ethylcellulose (15 mg) and water. The granules were then dried at 60° C. and passed through a 1 mm screen.

To the warmed tramadol containing granules was added molten cetostearyl alcohol (42 mg) and the whole was mixed thoroughly. The granules were allowed to cool and sieved through a 1.6 mm screen. Purified talc and magnesium stearate were added and mixed with the granules. The granules were then compressed into tablets.

The tablets were coated with a film coat having the formulation given below.

|  | mg/tablet |
|---|---|
| Hydropropylmethylcellulose Ph. Eur. 15 cps (Methocel E15) | 0.770 |
| Hydroxypropylmethylcellulose (Ph. Eur. 5 cps (Methocel E5) | 3.87 |
| Opaspray M-1-7111B (33% solids) | 2.57 |
| Polyethylene glycol 400 USNF | 0.520 |

-continued

|  | mg/tablet |
|---|---|
| Purified Talc Ph. Eur. | 0.270 |
| Purified Water Ph. Eur. | 55.52* |

*Remove during processing.

EXAMPLE 2

Tablets having the following formulation were prepared:

|  | mg/tablet |
|---|---|
| Tramadol hydrochloride | 100.0 |
| Lactose Ph. Eur. | 58.0 |
| Ethylcellulose USNF (Ethocel 45 CP) | 15.0 |
| Cetostearyl alcohol Ph. Eur. (Dehydag wax O) | 52.0 |
| Magnesium stearate Ph. Eur. | 2.00 |
| Purified talc Ph. Eur. | 3.00 |

A mixture of tramadol hydrochloride (100 mg), lactose (58 mg) and ethylcellulose (15 mg) was granulated whilst adding molten cetostearyl alcohol (52 mg) and the whole was mixed thoroughly. The granules were allowed to cool and sieved through a 1.6 mm screen. Purified talc and magnesium stearate were added and mixed with the granules. The granules were then compressed into tablets which were coated with a film coat having the formulation given in Example 1.

EXAMPLE 3

Film coated tablets were produced following the procedure described in Example 2 and having the following formulation:

|  | mg/tablet |
|---|---|
| Tramadol hydrochloride | 100.00 |
| Lactose Ph. Eur. | 70.50 |
| Hydroxyethylcellulose Ph. Eur. | 12.50 |
| Cetostearyl alcohol Ph. Eur. | 42.00 |
| Magnesium stearate Ph. Eur. | 2.00 |
| Purified talc Ph. Eur. | 3.00 |

In Vitro Dissolution Studies

In vitro dissolution studies were conducted on tablets prepared as described above. Results are given in Table 1.

TABLE 1

| | WT % TRAMADOL RELEASED | | |
|---|---|---|---|
| Time (h) | Example 1 | Example 2* | Example 3 |
| 1 | 39 | 35 | 43 |
| 2 | 52 | 47 | 60 |
| 4 | 67 | 62 | 84 |
| 8 | 82 | 78 | 97 |
| 12 | 90 | 86 | — |

*Measured on tablet core

In a trial involving 12 healthy volunteers the serum levels of tramadol following administration of one tablet according to Example 2 was found to be as illustrated in FIG. 1.

EXAMPLES 4 AND 5

Particles having the formulations given in Table II below were prepared by the steps of:

i. Placing the ingredients (a) and (c) (total batch weight 0.7 kg) in the bowl of a liter capacity Collette Gral Mixer (or equivalent) equipped with variable speed mixing and granulating blades;

ii. Mixing the ingredients at about 150–1000 rpm whilst applying heat until the contents of the bowl are agglomerated.

iii. Classifying the agglomerated material by passage through a Comil and/or Jackson Crockatt to obtain controlled release seeds.

iv. Warming and mixing the classified material in the bowl of a 10 liter Collette Gral, until uniform multiparticulates of the desired pre-determined size range are formed in yield of greater than 80%. This takes approximately 5 minutes.

v. Discharging the multiparticulates from the mixer and sieving them to separate out the multiparticulates collected between 0.5 and 2 mm aperture sieves.

TABLE II

| Example | 4 | 5 |
|---|---|---|
| (a) Tramadol HCl (Wt %) | 50 | 75 |
| (b) Hydrogenated Vegetable Oil (Wt %) | 50 | 25 |

EXAMPLE 6

Samples of the particles from Example 4 were blended with magnesium stearate and purified talc using a Y-Cone or bin-blender. The blended mixture was then compressed using either (1) 14×6 mm, (2) 16×7 mm or (3) 18.6×7.5 mm capsule shaped tooling on a single punch F3 Manesty tabletting machine to give tablets giving 200, 300 and 400 mg of tramadol HCl. The ingredients per dosage unit amounted to the following:

TABLE III

| TABLET | MG/TABLET | | |
|---|---|---|---|
| INGREDIENT | 1 | 2 | 3 |
| Tramadol HCl | 200 | 300 | 400 |
| Hydrogenated Vegetable Oil | 200 | 300 | 400 |
| Sub Total | 400 | 600 | 800 |
| Purified Talc | 12.63 | 18.95 | 25.26 |
| Magnesium Searate | 8.42 | 12.63 | 16.84 |

The tablets were assessed by the dissolution using Ph. Eur. Paddle Method 100 rpm, 0.1 N HCl.

To assess the non-compressed particles the Ph Eur. Paddle was replaced by a modified Ph Eur. Basket.

The results are shown in Table IV below;

TABLE IV

| HOURS AFTER START OF TEST | Particles | Tablet 1 | Tablet 2 | Tablet 3 |
|---|---|---|---|---|
| | % TRAMADOL HCl RELEASED | | | |
| 1 | 54 | 16 | 15 | 15 |
| 2 | 68 | 23 | 20 | 21 |
| 3 | 76 | 28 | 25 | 25 |
| 4 | 82 | 32 | 28 | 28 |
| 6 | 89 | 40 | 35 | 35 |
| 8 | 93 | 46 | 41 | 40 |
| 10 | 96 | 50 | 45 | 45 |
| 12 | 98 | 55 | 49 | 49 |
| 16 | 100 | 63 | 57 | 56 |
| 20 | NR | 70 | 63 | NR |

These results confirm the effectiveness of the tabletting in reducing the release rate.

EXAMPLE 7

Samples of the particles from Example 5 were then tabletted using a procedure similar to Example 3 and the ingredients per unit dosage amounted to:

TABLE V

| TABLET | MG/TABLET | | |
|---|---|---|---|
| INGREDIENT | 4 | 5 | 6 |
| Tramadol HCl | 200 | 300 | 400 |
| Hydrogeziated Vegetable Oil | 66.7 | 100 | 133 |
| Sub Total | 266.7 | 400 | 533 |
| Purified Talc | 7.63 | 11.44 | 15.25 |
| Magnesium Stearate | 5.16 | 7.63 | 10.17 |

The tablets and samples of non-compressed multiparticulates (each sample containing 400 mg of tramadol hydrochloride) were assessed by the dissolution method also described above. The results are shown in Table VI below;

TABLE VI

| HOURS AFTER START OF TEST | Particles | Tablet 4 | Tablet 5 | Tablet 6 |
|---|---|---|---|---|
| | % TRAMADOL HCl RELEASED | | | |
| 1 | 77 | 43 | 40 | 42 |
| 2 | 92 | 64 | 55 | 56 |
| 3 | 98 | 75 | 65 | 66 |
| 4 | 100 | 83 | 72 | 73 |
| 6 | 102 | 94 | 83 | 84 |
| 8 | 102 | 100 | 91 | 91 |
| 10 | 102 | NR | 96 | 97 |

These results show that by increasing the loading of the highly water soluble tramadol hydrochloride (75% w/w in this example compared with 50% w/w in Example 6) a significantly faster release rate of the active ingredient can be achieved.

EXAMPLE 8

Example 4 was repeated but with the following formulation:

| Tramadol HCl | 200 mg/tablet |
|---|---|
| Hydrogenated Vegetable Oil | 163.0 mg/tablet |

The resulting multiparticulates were blended as described in Example 6 with the following;

| Purified Talc | 11.5 mg/tablet |
|---|---|
| Magnesium Stearate | 7.66 mg/tablet |

The blend was then compressed as described in Example 6 but using 15 mm×6.5 mm normal concave capsule shaped plain/plain punches.

The resulting tablets were then assessed by the dissolution method described above. The results are shown in Table V.

| HOURS AFTER START OF TEST | % TRAMADOL HCl RELEASED |
|---|---|
| 1 | 20 |
| 2 | 27 |
| 3 | 32 |
| 4 | 37 |
| 6 | 44 |
| 8 | 50 |
| 10 | 55 |
| 12 | 60 |
| 16 | 67 |
| 20 | 73 |
| 24 | 77 |

Figure 2:
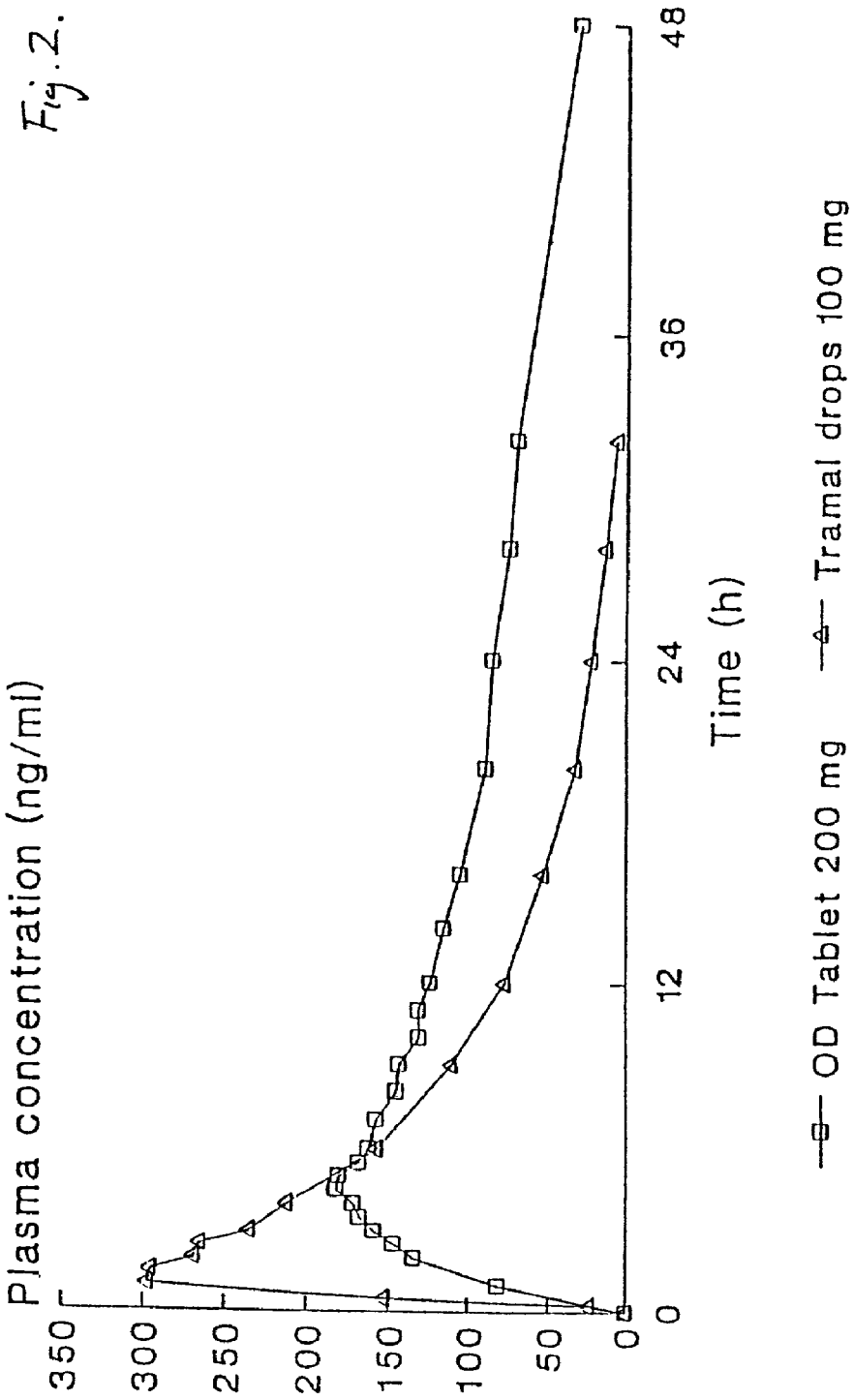
FIG. 2 is a graphical depiction of the plasma profile resulting from single dose administration of the tablet of Example 8 in comparison to the administration of a commercial preparation of tramadol drops 100 mg in a trial involving five healthy male volunteers.

In a trial involving five healthy male volunteers the plasma profile resulting from single dose administrations of the above tablet are shown in FIG. 2 in comparison to the administration of a commercial preparation of Tramadol drops 100 mg.

What is claimed is:

1. A solid controlled release oral dosage form, comprising,
a therapeutically effective amount of tramadol or a pharmaceutically acceptable salt thereof incorporated into a normal release matrix,
said matrix overcoated with a controlled release coating comprising a polymethacrylate or a water insoluble cellulose,
said dosage form providing a therapeutic effect for at least about 24 hours.

2. The controlled release dosage form as claimed in claim 1, wherein said controlled release coating comprises a polymethacrylate.

3. The controlled release dosage form as claimed in claim 1, wherein said controlled release coating comprises a water insoluble cellulose.

4. The controlled release dosage form as claimed in claim 2, wherein said controlled release coating further comprises a water soluble cellulose.

5. The controlled release dosage form as claimed in claim 3, wherein said controlled release coating further comprises a polyvinylpyrrolidone.

6. The controlled release dosage form as claimed in claim 1, containing from about 50 to 800 mg of tramadol or a pharmaceutically acceptable salt thereof, calculated as the hydrochloride salt.

7. The controlled release dosage form as claimed in claim 1, having a dissolution rate in-vitro when measured using the Ph. Eur. Paddle Method at 100 rpm in 900 ml 0.1N hydrochloric acid at 37° C. and using UV detection at 270 nm, from about 0 to about 50% tramadol released after 1 hour; from about 0 to about 75% tramadol released after 2 hours; from about 10 to about 95% tramadol released after 4 hours; from about 35 to about 100% after 8 hours; from about 55 to about 100% tramadol released after 12 hours; from about 70 to about 100% tramadol released after 16 hours; and greater than 90% tramadol released after 24 hours, by weight.

8. The controlled release dosage form as claimed in claim 1, having a dissolution rate in-vitro when measured using the Ph. Eur. Paddle Method at 100 rpm in 900 ml 0.1N hydrochloric acid at 37° C. and using UV detection at 270 nm, from about 0 to about 30% tramadol released after 1 hour; from about 0 to about 40% tramadol released after 2 hours; from about 3 to about 55% tramadol released after 4 hours; from about 10 to about 65% after 8 hours; from about 20 to about 75% tramadol released after 12 hours; from about 30 to about 88% tramadol released after 16 hours; from about 50 to about 100% tramadol released after 24 hours and greater than 80% tramadol released after 36 hours, by weight.

9. The controlled release dosage form as claimed in claim 1, having a dissolution rate in-vitro when measured using the Ph. Eur. Paddle Method at 100 rpm in 900 ml 0.1N hydrochloric acid at 37° C. and using UV detection at 270 nm, from about 15 to about 25% tramadol released after 1 hour; from about 25 to about 35% tramadol released after 2 hours; from about 30 to about 45% tramadol released after 4 hours; from about 40 to about 60% after 8 hours; from about 55 to about 70% tramadol released after 12 hours; and from about 60 to about 75% tramadol released after 16 hours, by weight.

10. The dosage form according to claim 1, which provides a $t_{max}$ from about 3 to about 6 hours.

11. The dosage form according to claim 1, which provides a $W_{50}$ from about 10 to about 33 hours.

12. The dosage form according to claim 3 wherein said water insoluble cellulose comprises ethylcellulose.

13. The dosage form of claim 1, comprising 100 mg tramadol hydrochloride.

14. The dosage form of claim 1, comprising 200 mg tramadol hydrochloride.

15. The dosage form of claim 1, comprising 300 mg tramadol hydrochloride.

16. The dosage form of claim 1, comprising 400 mg tramadol hydrochloride.

17. The dosage form of claim 1, comprising 600 mg tramadol hydrochloride.

* * * * *